United States Patent [19]

Sinha et al.

[11] Patent Number: 5,222,388
[45] Date of Patent: Jun. 29, 1993

[54] NITROGEN DIOXIDE DETECTION

[75] Inventors: Dipen N. Sinha; Stephen F. Agnew, both of Los Alamos, N. Mex.; William H. Christensen, Buena Park, Calif.

[73] Assignee: University of California Patent, Trademark & Copyright Office, Alameda, Calif.

[21] Appl. No.: 671,225

[22] Filed: Mar. 19, 1991

[51] Int. Cl.⁵ .............................................. G01N 27/00
[52] U.S. Cl. ..................................... 73/23.2; 73/31.05
[58] Field of Search ................. 73/23.2, 25.03, 31.05; 436/98; 338/34; 340/632

[56] References Cited

U.S. PATENT DOCUMENTS

| | | | |
|---|---|---|---|
| 2,728,831 | 12/1955 | Pope | 201/63 |
| 2,937,524 | 5/1960 | Gregor | 73/335 |
| 3,924,219 | 2/1975 | Braun | 338/34 |
| 4,142,400 | 3/1979 | Colla et al. | 73/23 |
| 4,225,842 | 7/1979 | Schlesselman et al. | 338/34 |
| 4,236,307 | 12/1980 | Colla et al. | 29/857 |
| 4,264,331 | 5/1981 | Klein et al. | 338/34 |
| 4,388,342 | 6/1983 | Suzuki et al. | 73/23.2 |
| 4,499,240 | 2/1985 | Valentine | 156/175 |
| 4,563,893 | 1/1986 | Tanyolac et al. | 73/31.05 |
| 4,579,921 | 4/1986 | Gouarderes et al. | 526/159 |
| 4,681,855 | 7/1987 | Huang | 436/39 |
| 4,755,473 | 7/1988 | Nishino et al. | 73/31.05 |
| 4,869,874 | 9/1989 | Falat | 422/53 |
| 5,018,380 | 5/1991 | Zupancic et al. | 73/23.2 |
| 5,049,808 | 9/1991 | Okahata | 73/24.06 |
| 5,071,626 | 12/1991 | Tuller | 338/34 |
| 5,085,776 | 2/1992 | Blume et al. | 55/158 |
| 5,135,637 | 8/1992 | Eida et al. | 252/351 |

FOREIGN PATENT DOCUMENTS

| | | | |
|---|---|---|---|
| 0127837 | 8/1982 | Japan | 73/31.05 |
| 0178346 | 9/1985 | Japan | 73/23.2 |
| 0256043 | 12/1985 | Japan | 73/31.05 |
| 0147145 | 7/1986 | Japan | 73/31.05 |
| 2166244 | 5/1986 | United Kingdom | 73/31.05 |

OTHER PUBLICATIONS

Los Alamos National Laboratory report La-UR-8-9-3251, (Jul. 1990), William H. Christensen et al., "Conductivity of Polystyrene Film Upon Exposure To Nitrogen Dioxide: A Novel $NO_2$ Sensor".

Primary Examiner—Herbert Goldstein
Assistant Examiner—Raymond Y. Mah
Attorney, Agent, or Firm—Richard J. Cordovano; Paul D. Gaetjens

[57] ABSTRACT

Method and apparatus for detecting the presence of gaseous nitrogen dioxide and determining the amount of gas which is present. Though polystyrene is normally an insulator, it becomes electrically conductive in the presence of nitrogen dioxide. Conductance or resistance of a polystyrene sensing element is related to the concentration of nitrogen dioxide at the sensing element.

10 Claims, 2 Drawing Sheets

NITROGEN DIOXIDE DETECTION

BACKGROUND OF THE INVENTION

This invention relates to electrochemical sensing and measurement. This invention is the result of a contract with the Department of Energy (Contract No. W-7405-ENG-36).

Nitrogen dioxide is a harmful pollutant and a component of urban smog. In order to reduce the amount of nitrogen dioxide in the atmosphere, it is necessary to detect and measure the concentration of the gas both in the atmosphere and in streams of gas discharged into the atmosphere. There are also industrial processes in which it is desirable to detect and measure nitrogen dioxide concentration. Desirable characteristics of nitrogen dioxide detection and measurement apparatus include selectivity for nitrogen dioxide, reversibility, low cost, low power requirement, rapid response, and a sensor which is robust and simple in design.

SUMMARY OF THE INVENTION

This invention is a method and apparatus for detecting the presence of gaseous nitrogen dioxide and determining the amount of gas which is present. Though polystyrene is normally an insulator, it becomes electrically conductive in the presence of nitrogen dioxide. Conductance or resistance of a polystyrene sensing element is related to the concentration of nitrogen dioxide at the sensing element.

DESCRIPTION OF THE INVENTION

Figure 1:
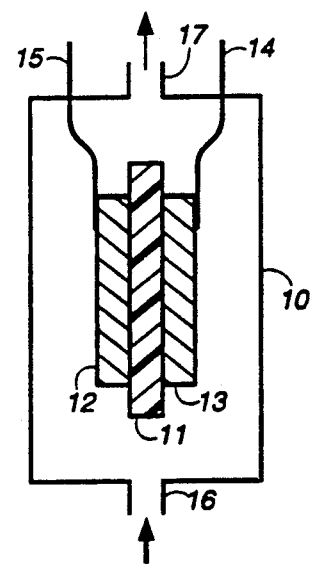
FIG. 1 is a schematic representation, in cross section, of a polystyrene sensing element having two electrodes in contact with it. This sensor is contained within a housing through which flows a gas stream monitored by the sensor.

As used herein, a sensing element is a polystyrene member and a sensor is comprised of a sensing element and electrodes and may be defined as the apparatus in contact with the gas stream. In the embodiment of FIG. 1, polystyrene sensing element 11 has a first surface in contact with electrode 12 and a second and opposing surface in contact with electrode 13. This sensor is contained in housing 10 and senses the presence of nitrogen dioxide ($NO_2$) in a gas stream which enters the housing through nozzle 16 and exits the housing through nozzle 17, as shown by the arrows. Electrical leads 14 and 15 are attached to the electrodes so that the conductance of sensing element 11 can be measured by connecting the free ends of the leads to conductance measuring apparatus (not shown). Direct current is used. The conductance of the polystyrene sensing element will be directly proportional to the quantity of nitrogen dioxide in the gas stream. It may be desirable to use porous metal electrodes so that the nitrogen dioxide can migrate through the electrodes to contact the polystyrene sensing element. The sensor need not be in a housing and can also be used to detect $NO_2$ in a non-flowing gas.

Figure 2:
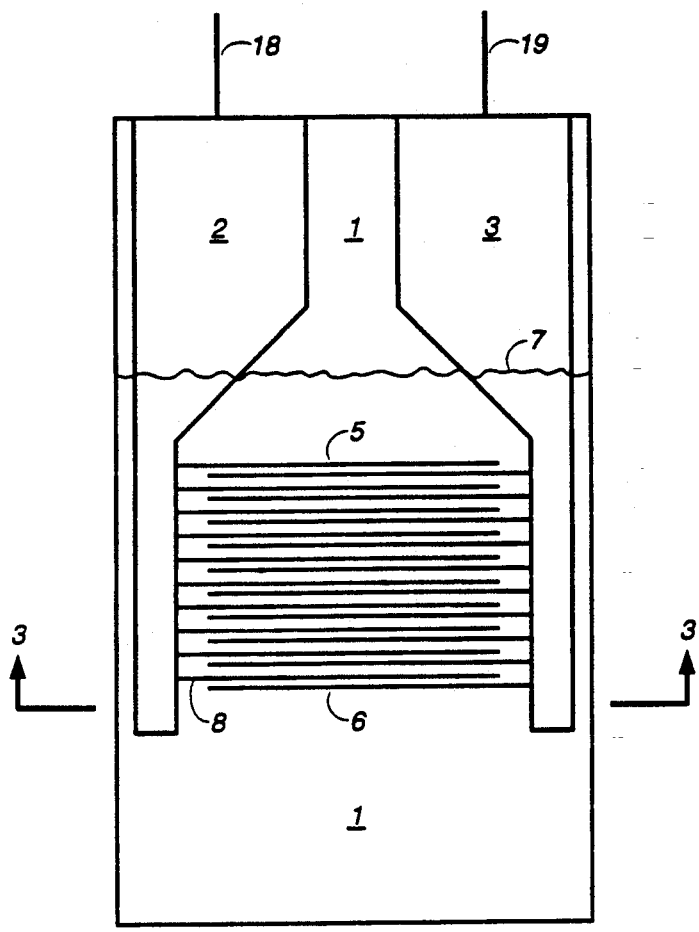
FIG. 2 is a schematic representation of a sensor having interdigitated electrodes. It is not drawn to scale.

FIG. 2 depicts a preferred embodiment of the sensor. Interdigitated electrodes mounted on a quartz substrate having a thickness of about 1 mm were purchased from Microsensor Systems, Inc. of Springfield, Va. (part no. 302). The substrate may be any insulating material which has a higher resistivity than polystyrene (when it is not exposed to $NO_2$). The substrate (with electrodes) was coated with polystyrene by dipping it into a solution of about 1-2% by volume polystyrene in benzene. The polystyrene was obtained from commercially available polystyrene rods which were cut into pieces and dissolved in benzene. After dipping the substrate (with electrodes) into the solution once, slowly withdrawing it, and then allowing it to dry, the thickness of the film was about 0.35 micron, as determined by a profilometer. The substrate was dipped into the polystyrene solution a second time, resulting in the film on top of the substrate having a thickness of about 0.85 micron. The lower part of the substrate, as shown in FIG. 2, is coated with polystyrene up to line 7.

Figure 3:
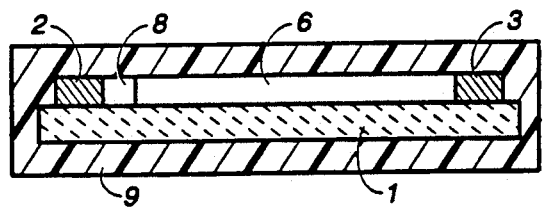
FIG. 3 is a section view of the sensor of FIG. 2 taken as shown by the section arrows of FIG. 2. It is not drawn to scale.

Referring now to both FIGS. 2 and 3, the substrate 1 has deposited on it electrodes 2 and 3, which are a thin gold film. Each electrode has 50 fingers, each having a width of 15 microns. The fingers are interdigitated with a distance between fingers of 15 microns. The area occupied by the 100 interdigitated fingers is 0.5 cm by 0.3 cm. The fingers are depicted in FIG. 2 by lines such as finger 5 of electrode 2 and finger 6 of electrode 3. Polystyrene coating 9 of FIG. 3 entirely surrounds substrate 1 and the electrodes. FIG. 3 shows electrodes 2 and 3 in section and the edge of finger 6. Between the end of finger 6 and electrode 2, the edge of finger 8 can be seen. Only the portions of the polystyrene between the fingers are important in its function as a sensing element. Electrical leads 18 and 19 are attached to the contact areas of electrode 2 and 3 so that the conductance of the polystyrene sensing element between electrodes 2 and 3 may be measured.

Use of interdigitated electrodes is preferred because the conductivity of polystyrene is quite small and these electrodes provide a large ratio of electrode perimeter (p) to electrode spacing (d) (p/d = 32,768). The conductance measured between the electrodes is related to conductivity by the equation $$c = d^p t \sigma$$

where $\sigma$ is in Siemans/cm, t = thickness of the sensing element, and c = conductance in Siemans. As can be seen from the equation, as p/d increases, the conductance increases. The ratio of p/d can be viewed as an inherent amplification factor.

In the experimentation, the sensor was mounted in a teflon block having gold pressure contacts and the leads were attached to a Keithley 616 digital electrometer. One of the electrodes was biased using a 1.45 volt mercury cell. Conductance data as a function of time were recorded with an IBM PC/AT computer equipped with a 12-bit analog to digital convertor. The sensor mounted in the teflon block was placed inside a glass housing with provisions for electrical leads to pass through the housing for connection to the electrometer. The housing was evacuated using a vacuum pump and nitrogen was added to bring the pressure inside the housing to 540 Torr. Nitrogen dioxide gas withdrawn from the cylinder containing liquid $N_2O_4$ was added to the housing to bring the pressure up to 600 Torr, thus producing a 10 vol % nitrogen dioxide in nitrogen atmosphere inside the housing.

Figure 4:
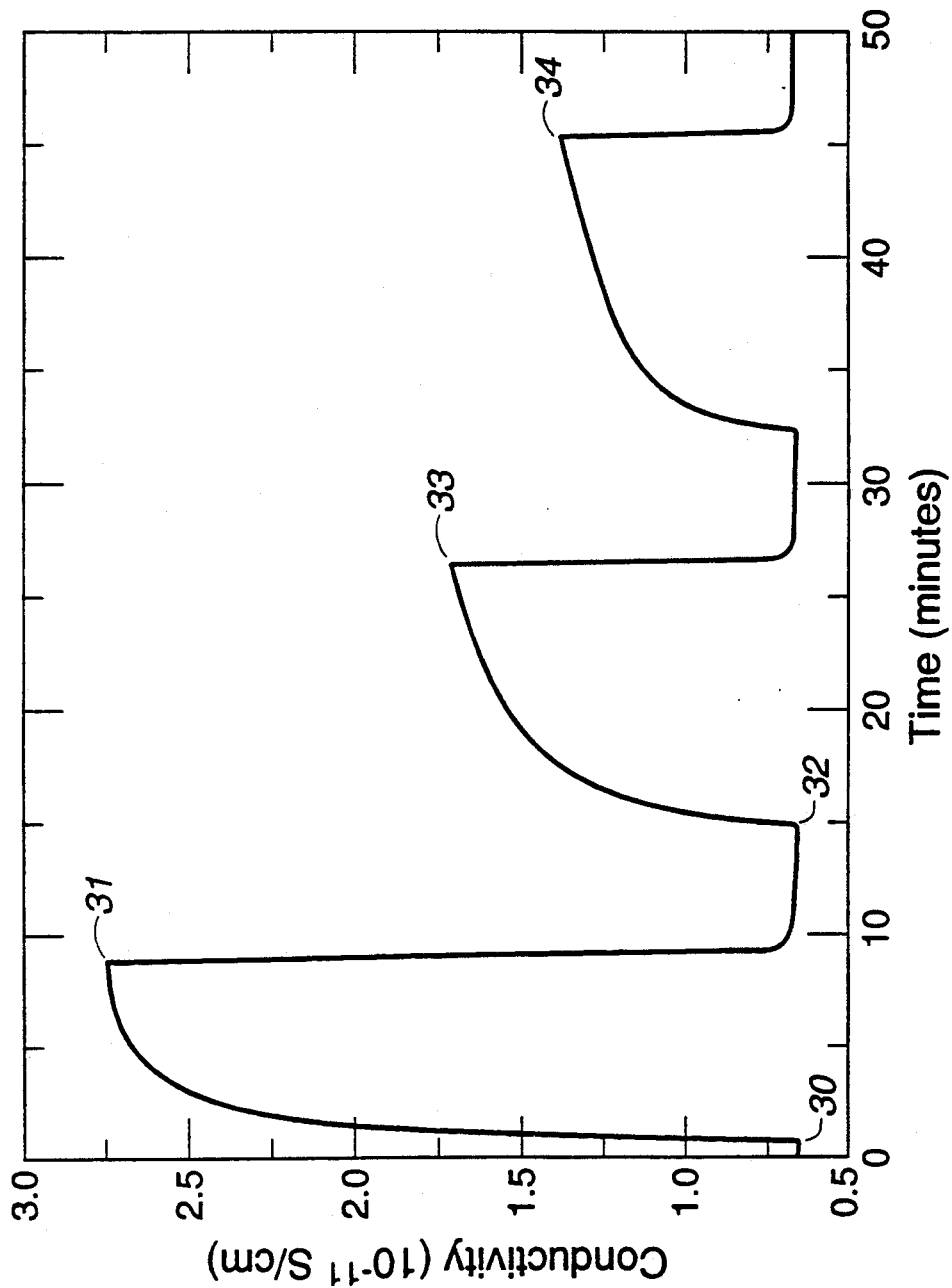
FIG. 4 shows the variation of conductivity with time of a sensor over three cycles of exposure to a gas containing nitrogen dioxide.

FIG. 4 shows the conductivity of a sensor in an experiment in which nitrogen dioxide was added to the housing and then removed from the housing by means of a vacuum pump. The cycle was repeated three times. Addition of nitrogen dioxide was started at point 30 and was completed within seconds. Conductivity of the sensing element increased to about $2.75 \times 10^{-11}$ S/cm in about 2 minutes. When the conductivity reached a constant value, the housing was evacuated and the conductivity instantly fell from the value at point 31 to its base value. At a time denoted by point 32, the housing was again filled with a 10% nitrogen dioxide mixture and the conductivity increased to a value of about $1.7 \times 10^{-11}$ S/cm, as shown at point 33. Evacuation and addition of a 10% nitrogen dioxide mixture was again accomplished with the conductivity rising to a peak value of about $1.3633 \, 10^{-11}$ S/cm, as shown by point 34. The baseline conductivity shown in the figure represents electronic noise. The conductance of the sensing element when not exposed to nitrogen dioxide was determined to be less than $1 \times 10^{-14}$ S/cm, that value being the lower limit of the electrometer range. The extremely rapid drop in conductivity upon evacuation of the housing is not due to the use of a vacuum pump to remove $NO_2$, but accurately reflects the response time of the sensor. This can be seen by establishing a flow through the housing of the $N_2/NO_2$ mixture and turning off the $NO_2$ supply valve: the conductance drops to its base value almost as rapidly as when the housing is evacuated.

The lack of repeatability shown in FIG. 4 is due to delamination of the sensing element from the electrodes. The reason for delamination is further discussed below. It is expected that the delamination problem will be solved by treating the electrodes with a chemical bonding agent having a strong affinity for both the electrode material and for polystyrene. The bonding agent reacts with the electrode surface to produce salt-like fragments which are covalently bound to the metal and also covalently bind to the polystyrene; thus, the two materials are very strongly adhered to one another. Two compounds which may be used as bonding agents are polystyrene dicarboxy-terminated, no. 18961-8, from Aldrich Chemical of Milwaukee and polystyrene allyl alcohol, no. 07774, from Polysciences, Inc. of Warrington, Pa. There are other graft polymers functionalized by adding carboxylate groups which may be used as bonding agents and compounds not based on polystyrene which may be used a bonding agents.

It is believed that the conductivity of the polystyrene sensing element is due to the self-ionization of $N_2O_4$, which is the form of $NO_2$ within the film. The ions transport electrical charge between the electrodes, where oxidation and reduction of the $N_2O_4$ is taking place. This is further discussed below.

As mentioned above, we used a mercury cell to bias one of the electrodes; then, current flowing through the sensing element was measured. This was done because the response time of the electrometer was slow when directly measuring film resistance. Though the response time of the electrometer was sufficiently fast with the biased electrode, the electrometer was sensitive to electrical noise, which can be seen in FIG. 4 as the low portion of the curve.

Sensors were exposed to air, air and water vapor, oxygen, ammonia, hydrogen, and nitrogen. The sensors did not respond to any of these substances. Also, there was no change in the conductance of a sensor when a 10 vol % nitrogen dioxide stream was humidified. Polystyrene is normally an insulator and it appears that it remains an insulator upon exposure to substances other than nitrogen dioxide, at least when the exposure duration is short. The effects of prolonged exposure (many days) on these and other materials has not been studied.

Polystyrene is a polymer whose repeat unit is styrene, which is also known as vinyl benzene, and has the chemical formula $C_6H_5CH=CH_2$. As used herein, detection generally means determining that nitrogen dioxide is present by measuring conductance but not determining the amount present or concentration.

Computer means or other less sophisticated means for performing calculations may be used to convert measured values of resistance or current or conductance to conductivity and to determine the concentrations of $NO_2$ which correspond to particular values of conductivity. Also, the sensor can be calibrated directly, so that a meter measuring conductance or resistance may have a scale which reads in concentration units.

Though the above has dealt with conductance as the parameter which is measured and used to obtain concentration of $NO_2$, resistance may also be so used, since resistance is the reciprocal of conductance. Also, current may be measured and related to conductance by means of Ohm's law.

An analog computational integrated circuit can be used to convert conductance to concentration values. A complete $NO_2$ detector which is very compact can be made; it would be comprised of a sensor and a small button type battery mounted on an integrated circuit package. Such a detector could be combined with a wireless transmitter; this would be useful for detecting $NO_2$ in the atmosphere at remote locations A compact multiple purpose sensor utilizing the present invention may be designed. It would use sensors for other gases, such as sulfur oxides and chlorine, of the same general type as the $NO_2$ sensor, which are mounted on a package containing integrated circuitry.

Existing $NO_2$ detectors, such as those based on pthalocyanine and indium-tin oxide, must be heated to a temperature of 300° to 400° C. in order to function. This means that a prior art sensor cannot be powered by a compact battery. The inventive sensor requires only a small amount of power and thus a detector using a small battery is feasible.

Though the conductivity of polystyrene will not vary greatly, if at all, it will be necessary to calibrate each sensor using known $NO_2$ samples. This is because it is not possible to manufacture sensors which are absolutely identical. Factors such as the quality of adhesion between metal and polystyrene, film thickness, and film uniformity will vary.

It is believed that other polymers having certain properties may also be useful as $NO_2$ sensors, such as polyvinyl alcohol and certain polyethers. The required properties are ability to form thin films and $NO_2$ solubility.

The interaction of $NO_2$ with polystyrene was studied using Fourier transform infrared absorption spectroscopy with a Digilab FTS-40 spectrometer. Gas was placed within a cell having two "windows" consisting of two films of polystyrene. The windows were parallel to each other, with the inside surface of each exposed to the gas and the exterior surfaces exposed to the atmosphere. Use of this cell allowed the exposure of films to the $NO_2/N_2$ mix and direct infrared observation of the films before, during, and following exposure. The primary form of $NO_2$ within the film is actually $N_2O_4$; no free $NO_2$ was observed. This is indicated by bands at 1251 and 1737 cm$^{-1}$, which compare with reported values for $N_2O_4$ in frozen matrices at 1261 and (1735,1750) cm$^{-1}$. These frequencies are clearly associated with $N_2O_4$ and not $NO_2$, whose reported bands are at 1318 (very weak) and 1612 cm$^{-1}$. Also, small amounts of $N_2O_3$ were observed within the film (bands at 1291 and 1836 cm$^{-1}$, compared with reported 1298 and 1861 cm$^{-1}$, although 1953 cm$^{-1}$ is not observed due to interference from polystyrene) presumably due to gas phase reactions of $NO_2$ with the inside of our stainless cell body. We considered the possibility that these latter bands were due to the nitrite isomer of $N_2O_4$, which has reported frequencies at 1829, 1645, and 1291 cm$^{-1}$. In spite of the fact that two of these features match better than did the $N_2O_3$, the lack of any intensity at 1645 cm$^{-1}$, where there is no interference from polystyrene, must mean that there is no isomer present. In addition, the $N_2O_3$ bands increased with time following exposure, as expected for a decomposition product resulting from reaction of $NO_2$ with various metal components of the cell.

These bands all disappeared completely upon evacuation, and returned whenever the cell was refilled with the $NO_2$ mixture. No chemical degradation of the film occurred (i.e., nitration of the polymer) for short exposures up to several hours, which is consistent with previous work by others, where only exposure of such films at elevated temperatures resulted in any measurable nitration product. However, overnight exposure ($\sim$12 hrs.) of these films to $NO_2$ did result in a small amount of nitration product as indicated by the irreversible appearance of bands 1276, 1347, 1521, 1567, and 1760 cm$^{-1}$. Polystyrene has a large affinity for $N_2O_4$ and that is key in the operation of this sensor.

We believe we understand how the sensor operates; this will help us increase both the sensitivity and lifetime of this sensor. The time dependence of the conductance following exposure of the film to $NO_2/N_2$ mixture is very similar to that expected from a concentration polarization of species associated with some kind of redox chemistry of $N_2O_4$. It rises very quickly at first, and then asymptotically approaches a limiting value. This behavior is very common in electrochemical cells and indicates that there are electrochemical processes generating charge carriers which are depleting the $N_2O_4$ in the vicinity of the electrodes. But how is the charge being transported through the film? This electrochemistry is, after all, occurring in an extremely non-polar hydrophobic thin film.

Much work has been reported on the self-ionization of $N_2O_4$ under a variety of conditions. This molecule represents an unusual example of self-ionization, since all other species that undergo self-ionization are polar to begin with, such as water, $AsF_5$, $PF_5$, and $H_2SO_4$. The $N_2O_4$ self-ionization reaction involves transformation of this non-polar molecule into nitrosonium nitrate, $NO^+ \cdot NO_3^-$. We believe that the transport of charge within the film is due to this self-ionization and propose the following cathodic and anodic processes:

Cathodic:

Anodic:

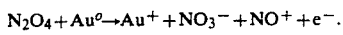

The bulk of the $N_2O_4$, then, provides a "salt bridge" through the polystyrene, enabling it to conduct nitrosonium and nitrate ions that are created at each of the electrodes. We have found no evidence for $NO_3^-$ ion in any of the films that we have exposed, although we are not yet able to examine a film that is actually undergoing electrochemistry. We believe nevertheless that incipient ion formation is responsible for charge migration in our polystyrene films.

Diminution of the measured conductance with subsequent exposures of the device to an identical $NO_2$ mixture are directly related to removal of $N_2O_4$ from the film. That is, during film exposure, the conductivity of the film actually slowly increases, showing no indication that is it degrading. Moreover, we have observed a diminution of film response and even no response with vigorous drying and elimination of residual benzene solvent from the film. We therefore attribute the diminished response to delamination of the film from the electrodes, which is induced by strains accompanying film swelling and deswelling.

Polystyrene's affinity for $N_2O_4$ is so large that absorption of $NO_2$ leads to swelling of the film and subsequent evacuation of $N_2O_4$ causes a sufficient strain in the film to separate it from the electrode surface.

We have ruled out various other explanations for the decrease in response of the device, such as chemical degradation (i.e., nitration), electrode corrosion, and other physical changes within the film (pore collapse, recrystallization, etc.). If any of these explanations were valid, we would expect that film conductance would decrease as some function of exposure time of the film to the $NO_2$ mixture. That is, exposure time would necessarily correlate with a decrease in conductance. Contrary to this, these phenomena are anti-correlated during film exposure to $NO_2$. Furthermore, since we do not observe any of the expected product bands in infrared spectra of films under similar conditions of exposure, we are even more certain of the lack of chemical degradation of the film. Finally, despite the fact that freshly cast films stick to the electrodes very strongly, the ease with which films are removed from the electrodes after experiments have been accomplished suggests that delamination is wholly responsible for the degradation in electrode response for subsequent exposures.

What is claimed is:

1. A method for detection of nitrogen dioxide in a gas comprising:
  a. exposing a sensing element consisting of polystyrene to said gas;
  b. imposing an electrical potential across said sensing element; and
  c. measuring the conductance or resistance of said sensing element.

2. The method of claim 1 further including converting said conductance or resistance value to an amount of nitrogen dioxide present in said gas.

3. Apparatus for detection of nitrogen dioxide in a gas comprised of:
  a. sensing element consisting of polystyrene having at least one pair of opposing surfaces, where the conductance and resistance of said sensing element do not vary in response to the presence in said gas of varying amounts of water vapor;

b. a first electrode having at least one surface in contact with a first of said sensing element opposing surfaces;

c. a second electrode having at least one surface in contact with a second of said sensing element opposing surfaces; and d. means for measuring the conductance or resistance of said sensing element between said electrodes.

4. The apparatus of claim 3 further including means for converting said conductance or resistance value to an amount of nitrogen dioxide present in said gas.

5. The apparatus of claim 3 where said electrodes are interdigitated electrodes and are encapsulated in polystyrene.

6. The apparatus of claim 3 where said electrodes are interdigitated electrodes disposed on an inert substrate and polystyrene is deposited on said substrate between fingers of said electrodes.

7. The apparatus of claim 3 where said sensing element is a thin film sandwiched between said first electrode and said second electrode.

8. The apparatus of claim 3 further including a housing containing said sensing element and said electrodes where said housing has a gas inlet nozzle and a gas outlet nozzle.

9. The apparatus of claim 3 where said electrodes are treated with a chemical bonding agent to prevent separation of said sensing element from the electrodes.

10. The apparatus of claim 3 where said electrodes are porous such that nitrogen dioxide gas can migrate through the electrodes to said sensing element.

* * * * *